United States Patent [19]

Rinehart et al.

[11] Patent Number: 5,569,757
[45] Date of Patent: Oct. 29, 1996

[54] 9-DEAZAADENOSINE AND ITS 5'-α-D-GLYCOPYRANOSIDE ISOLATED FROM THE CYANOBACTERIUM ANABAENA AFFINIS STRAIN VS-1

[76] Inventors: Kenneth L. Rinehart, 1306 S. Carle Ave., Urbana, Ill. 61801; Wayne W. Carmichael, 1331 Rise Rd., Yellow Springs, Ohio 45387; Michio Namikoshi, 1826 C Orchard Pl., Urana, Ill. 61801

[21] Appl. No.: 39,984

[22] Filed: Mar. 30, 1993

[51] Int. Cl.⁶ .............................. C12N 1/12; C12P 19/60
[52] U.S. Cl. .................. 536/17.4; 435/75; 435/257.1; 435/946; 536/16.8
[58] Field of Search .................... 536/17.4, 16.8; 435/257.1, 946, 75

[56] References Cited

PUBLICATIONS

J. Am Chem Soc. 1993, 115, pp. 2505–2507 Namikoshi et al.
Cover Sheet J. Am. Chem Soc. vol. 115 No. 4 Feb. 24, 1993. Grant No. AI 04769 to K. L. Rinehart and a subcontract from the same grant to W. W. Carmichael.
Townsend, L. B., Ed.; Chemistry of Nucleoside and Nucleotides, vol. 2 Plenum: New York 1991.
Otter, et al., J. Am. Chem. Soc., 114, 668–671 (1992).
J. Gilbert, Ecology, 71, 1727–1740 (1990)–culture strain sample received from Dr. Gilbert of Dartmouth College.
W. Carmichael, Fundamental Research in Homogeneous Catalysis; vol. 3, pp. 1249–1262, New York (1986).
J. Witten et al., Biochem. Biophys. Res. Commun. 124, 350–358 (1984).
Crow et al., Anal. Biochem., 139, 243–262 (1984).
E. Breitmaier et al., Carbon–13 NMR Spectroscopy; p. 289, VCH: Weinheim Germany, (1987).
Buchanan et al., J. Chem. Soc., Perkin Trans., 1, 195–202 (1991).
Chenon et al., J. Amer. Chem. Soc., 97, 4627–4636 (1975).
K. Imai, Chem. Pharm. Bull., 12, 1030–1042 (1964).
K. Anzai et al., J. Antibiot., Ser. A., 10, 201–204 (1957).
Bock et al., Advances in Carbohydrate Chemistry and Biochemistry vol. 41, pp. 27–66 (1983).
Stewart et al., J. Antibiot., 41, 1048–1056 (1988).
Lim et al., Tetrahedron Lett., 22, 25–28 (1981).

*Primary Examiner*—Herbert J. Lilling
*Attorney, Agent, or Firm*—Ernest V. Linek

[57] ABSTRACT

The present invention is based upon the discovery that a MeOH extract of *Anabaena affinis* strain VS-1 showed strong cytotoxicity to L1210 murine leukemia cells, and from that extract was isolated the compounds having the following structures, Compounds 1 and 2. These two compounds are believed to be responsible for the cytotoxicity of the marine organism. This is the first report of the isolation and characterization of pyrrolo[3,2-d] pyrimidine derivatives as biosynthetic products.

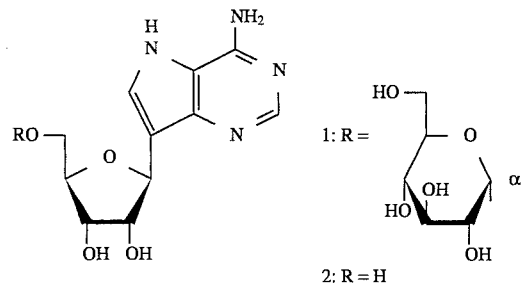

2 Claims, No Drawings

9-DEAZAADENOSINE AND ITS 5'-α-D-GLYCOPYRANOSIDE ISOLATED FROM THE CYANOBACTERIUM *ANABAENA AFFINIS* STRAIN VS-1

STATEMENT OF GOVERNMENT SUPPORT

This invention was supported by funds from the National Institute of Allergy and Infectious Diseases, Grant No. AI 04769.[1] Thus the government of the United States of America has certain rights in this invention.

BACKGROUND OF THE INVENTION

Numerous nucleoside analogs have been synthesized and isolated from natural sources, and their biological activities have also been extensively investigated. While it would be almost impossible to isolate a new type of base per se since synthetic efforts have effectively provided examples of most variations on the base unit,[2] it would be important to isolate as a natural product a base unit which had previously been obtained only by chemical synthesis.

SUMMARY OF THE INVENTION

In the course of the screening of antiviral, antifungal, antibacterial, and cytotoxic compounds from cyanobacteria (i.e., blue-green algae), the present inventors discovered that a methanol (MeOH) extract of *Anabaena affinis* strain VS-1 showed strong cytotoxicity to L1210 murine leukemia cells, and following work up as described below, the assignment of the following structures was made for the two isolated compounds, designated herein as Compounds 1 and 2, which are believed to be responsible for cytotoxicity of the organism. Thus, the present invention is directed to the following isolated compounds, and to the use thereof in pharmaceutical compositions.

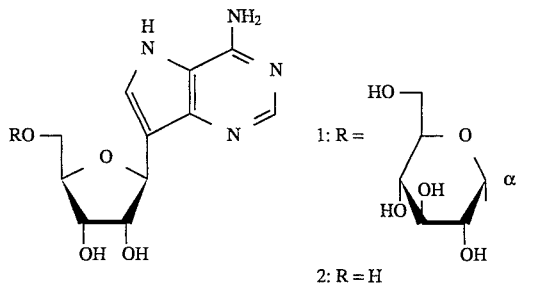

This is believed to be the first report of the isolation and characterization of pyrrolo[3,2-d] pyrimidine derivatives as biosynthetic products.[3]

DETAILED DESCRIPTION OF THE PREFERRED EMBODIMENT

*A. affinis* strain VS-1 was isolated from a cyanobacterial water-bloom collected from Star Lake, Norwich, Vt.[4] and cultivated in Z-8 mineral medium according to the conditions reported by Carmichael.[5] A sample of this cyanobacterium was deposited in the American Type Culture Collection (ATCC) on Apr. 8, 1996. It is available therefrom under Accession No. ATCC-55755. On Feb. 24, 1995, a sample of *Anabaena affinis* strain VS-1 was mailed for deposit to the UTEX Culture Collection of Algae, maintained by the Department of Botany at the University of Texas at Austin, Austin, Tex. 78713-7640, from which it is now available to the public (without restriction) by name (*A. Affinis*, VS-1).

For further information regarding this algae collection, see the Supplement to the *Journal of Phycology*, Vol. 29, No. 2 (April 1993). The lyophilized cells were extracted with MeOH-$H_2O$ (4:1), and the aqueous residue obtained after evaporation of the MeOH was passed through a CHP-20P column. The column was rinsed with $H_2O$, and the active components were eluted with 15% EtOH-$H_2O$ and evaporated. Two active components, Compound 1 (0.25% of dried cell weight) and Compound 2 (0.028%), were isolated by bioassay-guided separation of the residue using HPLC with an ODS column.[6]

Compound 1, $[\alpha]^{28}_D +21.9°$ (c0.051, $H_2O$), showed a molecular ion peak at m/z 429.1627 ($C_{17}H_{24}N_4O_9$, M+H, Δ-0.5 mDa) in the high-resolution (HR) FAB mass spectrum obtained with dithiothreitol/dithioerythritol (magic bullet)[7] as matrix. The $^1$H NMR spectrum of Compound 1 contained two aromatic proton signals and 13 one-proton signals ascribable to a pentose and a hexose.[8] Six heteroatom-substituted aromatic $^{13}$C signals were detected in the $^{13}$C NMR spectrum of Compound 1, together with 11 signals due to the sugar units.[9] These data and the UV spectrum of Compound 1 [$\lambda_{max}$ ($H_2O$) 287 (sh), 276, 268, and 229 nm; (0.01 n Hcl) 272 and 235 nm] suggested that Compound 1 is a nucleoside with two sugar units.

Collisionally induced tandem FABMS (FABMS/CID/MS) of Compound 1 showed three major fragment ion peaks at m/z 177, 163, and 147 (Scheme I), together with a strong fragment ion peak at m/z 267 generated by the loss of the hexose unit, but a prominent peak due to (base+$H_2$)$^+$ was not detected, suggesting a C-nucleoside,[10] This was confirmed by the chemical shift of the anomeric center ($\delta_H$, 4.87; δC, 78.1), which were observed at relatively high fields in the $^1$H and $^{13}$C NMR spectra of Compound 1.

SCHEME I

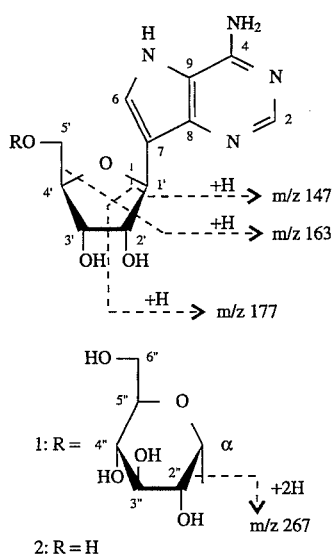

Subtraction of the sum of the two sugar units from the molecular formula of Compound 1 gave $C_6H_5N_4$ (133 Da) as the base unit. One-bond $^1$H-$^{13}$C coupling constants of $^{13}$C signals at δ 128.0 ($^1J_{C,H}$=190 Hz) and 149.9 ($^1J_{C,H}$=207 Hz) were characteristic for carbons attached to, respectively, one and two nitrogen atoms.[11] The $^1$H signal ($\delta_H$ 7.72) for the hydrogen attached to the former carbon ($\delta_C$ 128.0) showed long-range coupling (J=1.0 Hz) to an anomeric proton ($\delta_H$ 4.89, H-1'). These data suggested that the base unit is either pyrrolo[2,3-d]pyrimidine (i.e., 9-deazaadenine). The $^{13}$C signals due to the aromatic carbons of Compound 1 resemble those reported for 9-deazaadenine derivatives[12] rather than 7-deazaadenine derivatives,[13] although no pyrrolo[3,2-d] pyrimidine derivative has been reported from natural sources.[3] UV spectra of Compound 1, especially the shifts of absorption maxima in acidic solution, were also more like those of 9-deazaadenine[14] than those of tubercidin (7-deazaadenosine).[15] Accordingly, the base unit in Compound 1 is most likely 9-deazaadenine.

The $^{13}$C signals assigned to the hexose unit of Compound 1 closely resembled those of methyl α-D-glucopyranoside,[16] suggesting that Compound 1 is the α-D-glucopyranoside of 9-deazaadenosine. 5'-α-D-Glucopyranosides of tubercidin and toyocamycin (Compounds 3 and 4, respectively, Scheme II) have been isolated from cyanobacteria.[17] $^1$H and $^{13}$C NMR data for the sugar units of Compound 1 were very similar to those for Compounds 3 and 4, except for the signals due to the C-1' position. Moreover, enzymatic deglycosidation of Compound 1 with α-D-glucosidase gave D-glucose and Compound 2, which was isolated as the minor component (11% of Compound 1) from the same cyanobacterium.

SCHEME II

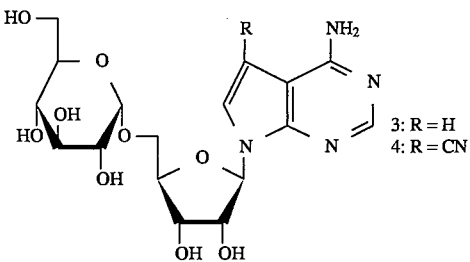

3: R = H
4: R = CN

Compound 2, $[\alpha]^{28}_D$ −28.4° (C 0.016 H$_2$O), showed a molecular ion peak at m/z 267.1090 (C$_{11}$H$_{15}$N$_4$O$_4$, M+H, Δ+0.3 Mda) by HRFABMS. FABMS/CID/MS of Compound 2 gave the same fragment ion peaks at m/z 177, 163 and 147 observed for Compound 1 (Scheme I). The $^1$H NMR spectrum of Compound 2 showed the signals ascribable to a ribose unit and two aromatic proton signals.[18]

From the results above, the structure of Compound 2 can be assigned as 9-deazaadenosine, which has been synthesized by Lim and Klein as a cytotoxic C-nucleoside isostere of adenosine.[19] The direct comparison of Compound 2 with a synthetic sample of 9-deazaadenosine[20] by HPLC, TLC, and UV spectra confirmed that Compound 2 was identical to synthetic 9-deazaadenosine. [6] $^1$H NMR data for natural Compound 2 hydrochloride were also identical with those for synthetic Compound 2 hydrochloride.[21]

Consequently, the structure of Compound 1 was assigned as the 9-deazaadenosine 5'-α-D-glucopyranoside, as shown in Scheme I. Compounds 1 and 2 are pyrrolo[3,2-d]pyrimidine derivatives which have not been reported previously as biosynthetic products,[3] i.e., from natural sources. Their biosynthesis will be of considerable interest.

The IC$_{50}$s of Compounds 1 and 2 vs L1210 murine leukemia cells were 0.01 and 0.002 μg/mL, respectively. These compounds also showed lethal toxicity to the aquatic invertebrate Ceriodaphnia dubia; the LC$_{50}$s for acute (48 hr) and chronic (7 day) toxicities were, respectively, 0.5 and 0.3 μg/mL for Compound 1 and 0.3 and 0.1 μg/mL for Compound 2. Thus, these compounds are expected to be useful as pharmaceutical agents in mammals, including humans.

FOOTNOTES & REFERENCES (1) Grant No. AI 04769 to K. L. Rinehart and a subcontract from the same grant to W. W. Carmichael.

(2) Chemistry of Nucleoside and Nucleotides; Townsend, L. B., Ed.; Plenum: New York 1991; Vol. 2.

(3) Otter, B. A.; Patil, S. A.; Klein, R. S.; Ealick, S. E., J. Am. Chem. Soc., 1992, 114, 668–671.

(4) Gilbert, J. J., Ecology, 1990, 71, 1727–1740; culture strain sample received from Dr. Gilbert of Dartmouth College.

(5) Carmichael, W. W., in Fundamental Research in Homogeneous Catalysis; Shilo, V., Ed.; Gordon and Breach: New York, 1986; Vol. 3, pp 1249–1262.

(6) HPLC retention times (min. Nucleosil 7 C$_{18}$, 10 mm×250 mm, 2 mL/min) for Compounds 1 and 2, respectively; MeOH-0.5% AcOH (1:9), 11.1 and 13.1; MeOH-0.05% TFA (1:9) 17.8 and 21.3; MeCN-0.1% NH$_4$OAc (1:20), 15.4 and 20.2 TLC (R$_f$ value, silica gel, 0.25-mm thick) and Compounds 1 and 2, respectively: CHCl$_3$-MeOH-H$_2$O (26:15:3) 0.18 and 0.63; EtOAc-2-OrOH-H$_2$O (4:3:2), 0.24 and 0.50; 1-BuOH-AcOH-H$_2$O (4:1:1), 0.20 and 0.40.

(7) Witten, J. L.; Schaffer, M. H.; O'Shea, M.; Cook. J. S.; Hemling. M. E.; Rinehart, K. L., Jr., Biochem. Biophys. Res. Commun., 1984, 124, 350–358.

(8) $^1$H NMR data (500 MHz, 26° C.) for Compound 1 in DMSO-d$_6$ (2.40 ppm); δ 8.05 (s, H-2), 7.72 (d, J=1.0 Hz, H-6), 4.87 (d, J=5.0 Hz, H- 1'), 4.74 (d, J=3.5 Hz, H-1"), 4.25 (dd, J=5.0, 5.0 Hz, H-2'), 4.06 (dd, J=5.0, 4.5 H-5'), 3.59 (dd, J=11.5, 2.0 Hz, H-6"), 3.52 (dd, J=11.0, 3.0 Hz, H- 5'), J=9.0, 5.5, 2.0 Hz, H-5"), 3.23 (dd, J=9.5, 3.5 Hz, H-2"), 3.08 (dd, J=9.0, 9.0 Hz, H-4"), all signals for 1H; assigned by $^1$H-$^1$H COSY and single-frequency decoupling experiments.

(9) $^{13}$C NMR data (125 MHz, 26° C.) for Compound 1 in DMSO-d$_6$ (39.5 ppm); δ 150.8 (s), 149.9 (d, $^1J_{C,H}$=207 Hz, C-2), 144.4 (s), 128.0 (d, $^1J_{C,H}$=190 Hz, C-6) 114.2 (s), 114.1 (s), 98.7 (d, C-1"), 81.8 (d, C-4'), 78.1 (d, C-1'), 74.9 (d, C-2'), 73.4 (d, C-3'), 72.8 (d, C-5"), 72.3 (d, C-2"), 70.9 (d, C-3"), 70.1 (d, C-4"), 66.9 (t, C-5'), 61.0 (t, C-6"); assigned by $^1$H-$^{13}$C COSY experiment.

(10) Crow, F. W.; Tomer, K. B.; Gross, M. L.; McCloskey, J. A.; Bergstrom, D. E., Anal. Biochem., 1984, 139, 243–262.

(11) Breitmaier, E.; Voelter, W., Carbon-13 NMR Spectroscopy; VCH: Weinheim, Germany, 1987; p. 289.

(12) Buchanan, J. G.; Craven, D. A.; Wightman, R. H.; Harnden, M. R., J. Chem. Soc., Perkin Trans., 1, 1991, 195–202.

(13) Chenon, M. T.; Pugmire, R. J.; Grant, D. M.; Panzica, R. P.; Townsend, L. B., J. Amer. Chem. Soc., 1975, 97, 4627–4636.

(14) Imai, K., Chem. Pharm. Bull., 1964, 12, 1030–1042.

(15) Anzai, K.; Nakamura, G.; Suzuki S., J. Antibiot., Ser. A, 1957, 10, 201–204.

(16) Bock, K., Pedersen, C., in Advances in Carbohydrate Chemistry and Biochemistry; Tipson, R. S.; Horton, D., Eds.; Academic: New York, 1983; Vol. 41, pp 27–66.

(17) Stewart, J. B.; Bornemann, V.; Chen, J. L.; Moore, R. E.; Caplan, F. R.; Karuso, H.; Larsen, L. K.; Patterson, G. M. L., J. Antibiot., 1988, 41, 1048–1056. The assignments of $^1$H and $^{13}$C signals for the C-3" and 4" positions must be interchanged.

(18) $^1$H NMR data (500 MHz, 18° C.) for Compound 2 in DMSO-d$_6$ (2.49 ppm); δ 11.95 (1H, br s, NH), 8.17

(1H, s, H-2), 7.72 (2H, br s, NH$_2$), 7.58 (1H, s, H-6), 4.85 (1H, d, J=3.1 Hz, OH), 4.77 (1H, d, J=7.4 Hz, H-1'), 4.22 (1H, dd, J=7.4, 5.1 Hz, H-2'), 4.14 (1H, d, J=3.9 Hz, OH), 4.00 (1H, dd, J=5.1, 2.8 Hz, H-3'), 3.86 (1H, ddd, J=3.1, 3.1, 2.8 Hz, H-4'), 3.60 (1 h, dd, J=12.0, 3.1 Hz, H-5'), 3.51 (1H, dd J=12.0, 3.1 Hz, H-5'); assigned by single-frequency decoupling experiments.

(19) Lim, M. I.; Klein, R. S., *Tetrahedron Lett.*, 1981, 22, 25–28.

(20) The synthetic sample of 9-deazaadenosine hydrochloride was provided by Dr. Robert S. Klein, Montefiore Medical Center.

(21) $^1$H NMR data (500 MHz, 18° C.) for Compound 2 hydrochloride in DMSO-d$_6$ (2.49 ppm): δ 12.80 (1H, s, NH) 9.03 and 8.99 (each 1H, s, NH$_2$), 8.50 (1H, s, H-2), 7.86 (1H, d, J=1.0 Hz, H-6), 4.86 (1H, d, J=7.0 Hz, H-1'), 3.97 (1H, dd, J=7.0, 5.1 Hz H-3'), 3.94 (1H, dd, J=5.1, 3.1 Hz, H-2'). 3.87 (1H, dt, J=3.2, 3.1 Hz, H-4'), 3.62 (2H, d, J=3.2 Hz, H$_2$- 5').

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. The compound having the formula 1:

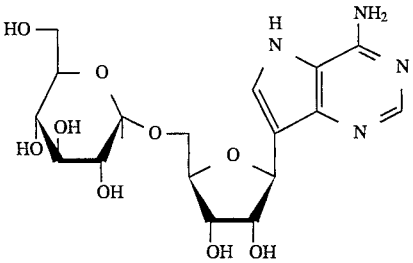

substantially free of the cellular debris of the blue-green algae, *Anabaena affinis*, Strain VS-1.

2. A pharmaceutical composition comprising the compound of claim 1 and a pharmaceutically acceptable carrier, diluent or excipent.

* * * * *